(12) United States Patent
Cullen

(10) Patent No.: US 7,794,925 B2
(45) Date of Patent: Sep. 14, 2010

(54) DIAGNOSIS OF CLINICAL INFECTION OF A WOUND

(75) Inventor: Breda Mary Cullen, North Yorkshire (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 296 days.

(21) Appl. No.: 10/494,507

(22) PCT Filed: Nov. 5, 2002

(86) PCT No.: PCT/GB02/05023

§ 371 (c)(1),
(2), (4) Date: Jul. 20, 2004

(87) PCT Pub. No.: WO03/040406

PCT Pub. Date: May 15, 2003

(65) Prior Publication Data

US 2005/0079542 A1 Apr. 14, 2005

(30) Foreign Application Priority Data

Nov. 5, 2001 (GB) ................................. 0126534.7

(51) Int. Cl.
*C12Q 1/00* (2006.01)
(52) U.S. Cl. .......................................... 435/4; 436/518
(58) Field of Classification Search ................. 436/518, 436/514–517, 104, 548, 164, 800, 805; 435/4–7.95, 435/283.1–289.1; 422/50–73; 356/4.01, 356/302, 303, 346
See application file for complete search history.

(56) References Cited

U.S. PATENT DOCUMENTS 5,912,114 A * 6/1999 Hutchinson et al. ............ 435/4
6,740,499 B2 * 5/2004 Sethi et al. ..................... 435/24

FOREIGN PATENT DOCUMENTS

| EP | 0 886 140 A1 | 12/1998 |
| GB | 232 3166 A | 9/1998 |
| WO | WO 00/08203 A1 | 2/2000 |

OTHER PUBLICATIONS

Grinnell et al., "Fibronectin Degradation in Chronic Wounds Depends on the Relative Levels of Elastase, alpha1-Proteinase Inhibitor, and alpha2-Macroglobulin", The Journal of Investigative Dermatology, vol. 106, No. 2, Feb. 1996.*

Merriam Webster's Collegiate Dictionary, Tenth Edition, 1996, "wound".*
Adachi, Y., et al., "Lpopolysaccharide increases fibronectin production and release from cultured lung fibroblasts partially through proteolytic activity," *J. of Lab. Clin. Med.*, 1996, 127(5), 448-455.
Bratschitsch, G., et al., "Clinical benefit of PMN-elestase as a determinant of inflammation signs for prospective wound healing monitoring after surgical emergency management," *Acta Chir. Austriaca*, 1997, Suppl. NR 133, 29-31.
Hofer, H.P., et al., "Released PMN elastase: an indicator of postsurgical uneventful wound healing and early inflammatory complications. A contribution to the search for objective criteria in wound healingmonitoring," *Injury*, 1995, 26(2), 103-106.
Hofer, H.P., et al., "Biochemical wound monitoring. PMN elastase in different healing stages after trauma surgery-orthopedic interventions," *Der Unfallchirurg*, 1993, 96(6), 292-298 (Abstract only).
Hofer, H.P., et al., "Released PMN elastase: an indicator of postsurgical uneventful wound healing and early inflammatory complications. A contribution to the search for objective criteria in wound healing monitoring," *Injury*, 1995, 26(2) 103-106 (Abstract only).
Fägerstam, L.G., et al., "Biosensor techniques," *Immunochemistry*, Van Oss, C.J. (Ed.), 1994, 949-970.
Gumenyuk, S.E., et al., "Method for predicting and early diagnosing postoperative soft tissue wound infectious complications involving determination of neutrophil activation, myeloperoxidase activity, albumin concentration and nuclear chromatin condensation in neutrophils from peripheral and wound blood," *Chem. Abstract No. 135:240382 and RU 2146367C1*, Year not available, (Abstract only).
Nwomeh, B.C., et al., "Physiology of chronic wound," *Clinics in Plastic Surgery, W.B. Saunders Co.*, 1998, 25(3), 341-356.
Tarlton, J.F., et al., "Postsurgical wound progression monitored by temporal changes in the expression of matrix metalloproteinase-9," British *J. of Dermatology*, 1997, 137(4), 506-516.
Yager, et al., "Ability of chronic wound fluids to degrade peptide growth factors is associated with increased levels of elastase activity and diminished levels of proteinase inhibitors," *Wound Re. Reg.*, 1997, 1(5) 23-32.

* cited by examiner

*Primary Examiner*—Ann Y Lam
(74) *Attorney, Agent, or Firm*—Morgan, Lewis & Bockius LLP

(57) ABSTRACT

A method of predicting or diagnosing clinical infection of a wound comprising measuring the concentration of a marker associated with an inflammatory response in wound fluid, wherein the marker is a fibronectin fragment, a neutrophil protease or a macrophage protease. Also provided is a use of a wound dressing or biosensor comprising components of an assay system for measuring the concentration of a marker associated with an inflammatory response, wherein the marker is a fibronectin fragment, a neutrophil protease or a macrophage protease, for use in the manufacture of a medicament for predicting the likelihood of clinical infection of the wound or for diagnosing clinical infection of a wound.

10 Claims, 1 Drawing Sheet

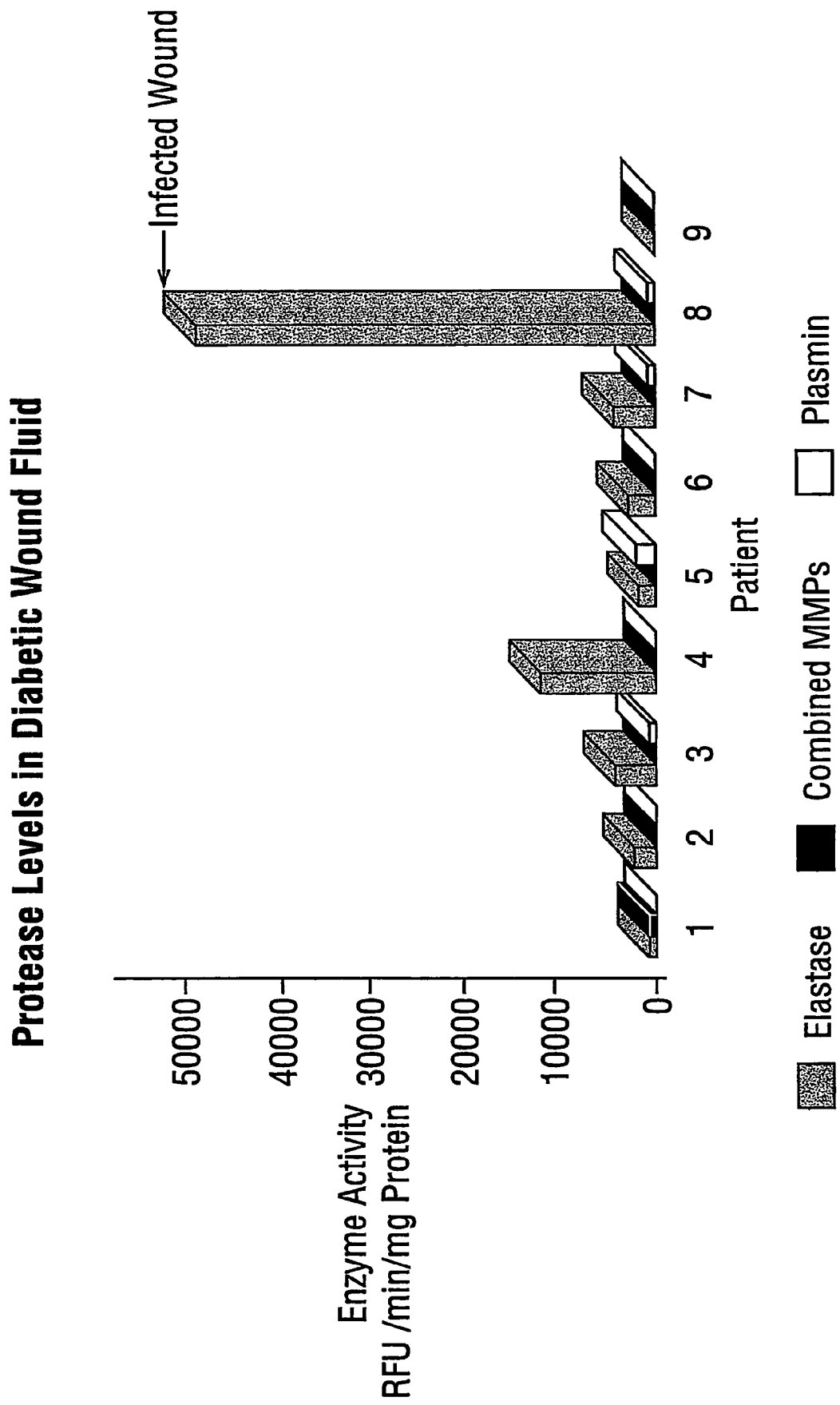

DIAGNOSIS OF CLINICAL INFECTION OF A WOUND

CROSS-REFERENCE TO RELATED APPLICATIONS

This application is the national stage filing under 35 U.S.C. §371 of International Application No. PCT/GB02/05023 filed Nov. 5, 2002 and published May 15, 2003, as International Publication No. WO 03/040406 which in turn claims priority under 35 U.S.C. §119 to Great Britain Patent Application No. 0126534.7, filed Nov. 5, 2001.

FIELD OF THE INVENTION

The present invention relates to a method of predicting or diagnosing clinical infection of a wound comprising measuring the concentration of a marker associated with an inflammatory response in wound fluid, for example the concentration of a neutrophil or macrophage protease. The present invention also relates to devices and kits for use in such methods.

BACKGROUND OF THE INVENTION

In mammals, injury triggers an organised complex cascade of cellular and biochemical events that result in a healed wound. Wound healing is a complex dynamic process that results in the restoration of anatomic continuity and function; an ideally healed wound is one that has returned to normal anatomic structure, function and appearance.

Infection of wounds by bacteria delays the healing process, since bacteria compete for nutrients and oxygen with macrophages and fibroblasts, whose activity are essential for the healing of the wound. Infection results when bacteria achieve dominance over the systemic and local factors of host resistance. Infection is therefore a manifestation of a disturbed host/bacteria equilibrium in favour of the invading bacteria. This elicits a systemic septic response, and also inhibits the multiple processes involved in wound healing. Lastly, infection can result in a prolonged inflammatory phase and thus slow healing, or may cause further necrosis of the wound. The granulation phase of the healing process will begin only after the infection has subsided.

The persistent presence of bacteria in injured tissue results in the prolonged elevation of proinflammatory cytokines such as interleukin-1 and tumour necrosis factor alpha (TNF-α). This in turn causes increases in the levels of matrix metalloproteinases, a decreased level of tissue inhibitors to the metalloproteinases (TIMP), and a decreased production of growth factors.

Chronically contaminated wounds all contain a tissue bacterial flora These bacteria may be indigenous to the patient or might be exogenous to the wound. Closure, or eventual healing of the wound is often based on a physician's ability to control the level of this bacterial flora.

Current methods used to identify bacterial infection rely mainly on judgement of the odour and appearance of a wound. With experience, it is possible to identify an infection in a wound by certain chemical signs such as redness or pain. Some clinicians take swabs that are then cultured in the laboratory to identify specific organisms, but this technique takes time. The prior art also describes the use of certain proteases as an indicator of healing status.

If clinicians could respond to wound infection as early as possible the infection could be treated topically as opposed to having to use antibiotics. This would also lead to less clinical intervention/hospitalisation and would reduce the use of antibiotics and other complications of infection.

There is thus a long felt need for a prognostic aid that would assist in predicting clinical infection of a wound prior to obvious clinical symptoms of infection. Such a prognostic aid would allow early intervention with suitable treatment (e.g. a topical antimicrobial treatment) before wound chronicity sets in. There is also a need for a diagnostic aid that would assist in the early diagnosis of clinical infection, preferably allowing diagnosis prior to obvious clinical symptoms of infection.

BRIEF DESCRIPTION OF THE DRAWINGS

FIG. 1 shows the levels of various proteases in diabetic wound fluid. Protease levels including elastase has been corrected for total protein present in the wound fluid sample, thus data is presented as RFU/min/mg protein (relative fluorescence units per minute-rate of change of fluorescence). Patient 8 had 10-fold more elastase activity and within two days was hospitalised for severe cellulitis/infection.

DETAILED DESCRIPTION OF THE INVENTION

It has been discovered that wound fluid from wounds that are apparently not clinically infected but which go on to become infected within a few days have high levels of neutrophil elastase activity and may also have high levels of other inflammatory proteases, such macrophage proteases and other neutrophil proteases. Similarly, the concentration of fibronectin fragments may also provide a useful indication of the likelihood of subsequent clinical infection; the presence of such fragments in chronic wounds being mainly due to high levels of elastase activity.

According to the present invention, there is provided a method of predicting or diagnosing clinical infection of a wound comprising measuring the concentration of a marker associated with an inflammatory response in wound fluid, wherein the marker is a fibronectin fragment, a neutrophil protease or a macrophage protease.

Also provided is a use of a wound dressing or biosensor comprising components of an assay system for measuring the concentration of a marker associated with an inflammatory response, wherein the marker is a fibronectin fragment, a neutrophil protease or a macrophage protease, for use in the manufacture of a medicament for predicting the likelihood of clinical infection of the wound or for diagnosing clinical infection of a wound.

Examples of neutrophil/macrophage proteases include elastase, MMP-9, MMP-8, MMP-1, MMP-12 and cathepsin G. Further examples include: collagen propeptide, a collagen telopeptide, a protease inhibitor, plasmin, lactate dehydrogenase, a cathepsin, a cytokine, a peroxidase enzyme, a cortisol free radical or a growth factors. More preferably, the marker is a protease enzyme selected from the group consisting of matrix metalloproteinases (e.g. MMP-9), neutrophil elastase, plasmin, low molecular weight gelatinases and latent or active elastases, interleukin converting enzymes or tumor necrosis factor (TNFα) converting enzymes.

By "measuring the concentration of a marker associated with an inflammatory response in wound fluid" we include measuring the activity of a marker associated with an inflammatory response in wound fluid. The term "wound fluid" refers to any wound exudate or other fluid (preferably substantially not including blood) that is present at the surface of the wound, or that is removed from the wound surface by aspiration, absorption or washing. The term "wound fluid" does not refer to blood or tissue plasma remote from the wound site.

It will be appreciated that the concentration of more than one marker may be measured. In certain embodiments, the concentrations of at least two, three or four markers are monitored.

Measuring the concentration of a marker associated with an inflammatory response in wound fluid allows the likelihood of (or the presence of) clinical infection to be assessed. The step of measuring is preferably carried out on wound fluid that has been removed from the body of the patient, but can also be performed on wound fluid in situ.

Any type of wound may be diagnosed for infection according to the method/use of the present invention. For example, the wound may be an acute wound such as an acute traumatic laceration, perhaps resulting from an intentional operative incision, or the wound may be a chronic wound. The method/use of the invention is envisaged as being most useful in predicting or diagnosing clinical infection of a chronic wound. Preferably, the chronic wound is selected from the group consisting of venous ulcers, pressure sores, decubitis ulcers, diabetic ulcers and chronic ulcers of unknown aetiology. Chronic wound fluids inherently have levels of markers such as neutrophil elastase that are many times the level found in normal, acute wound fluids. Nevertheless, it has now been found that the levels of such markers are further elevated by a substantial amount when the chronic wound will become infected.

According to the present invention, the prognostic/diagnostic assay is designed so as to provide a correlation between a given concentration of a marker of an inflammatory response and the likelihood of (or presence of) clinical infection.

Those skilled in the art will readily be able to determine concentration levels of markers of the inflammatory response, which are indicative of subsequent progression to clinical infection and/or of the presence of clinical infection. Preferably, a concentration at least 1.5-, 2-, 2.5-, 3.0-, 3.5-, 4.0-, 4.5-, 5.0-, 5.5-, 6.0-, 7.0-, 8.0- or 9.0-fold the basal level of the marker is considered as begin indicative of subsequent progression to clinical infection. By "measuring the concentration of a marker associated with an inflammatory response" we also include techniques that produce a positive or negative signal if the marker is present at one or more of these concentrations.

Preferably, a concentration at least 1.5-, 2-, 2.5-, 3.0-, 3.5-, 4.0-, 4.5-, 5.0-, 5.5-, 6.0-, 7.0-, 8.0-, 9.0-, 10.0-, 11.0-, 12.0- 14.0-, 16.0-fold the basal level of the marker is considered as begin indicative of the presence of clinical infection. By "measuring the concentration of a marker associated with an inflammatory response" we also include techniques that produce a positive or negative signal if the marker is present at one or more of these concentrations.

By the "basal level of the marker" we include the level of the marker normally associated with a wound which is not clinically infected and which does not subsequently become clinically infected. It will be appreciated that the basal level of the marker may be much higher for a chronic wound than for a normal, acute wound.

With regard to the concentration of neutrophil elastase which is associated with subsequent progression to clinical infection, our data indicates that an enzyme activity of at least 3,000 mg/min is indicative of the wound subsequently becoming clinically infected.

As used herein, the term wound fluid is meant to refer to the exudate that is secreted or discharged by cells in the environment of the wound. This fluid contains cells, both living and dead, and a variety of inflammatory cytokines.

By the "concentration of a marker of an inflammatory response" is meant the free concentration of the marker in the wound fluid. The concentration of the marker may be assessed in situ, or alternatively a sample of wound fluid may be taken as a clinical swab or as a fluid sample.

The concentration of the marker of the inflammatory response may be measured by any method known to those of skill in the art. Suitable methods include those utilising chemical or enzyme-linked reactions, or immunological (e.g. ELISA, western blots), spectrophotometric, calorimetric, fluorimetric, or radioactive detection based techniques. In one embodiment the concentration of the marker is measured by a dip-stick type test. Such a test could be used in the community and by the patient allowing easier and earlier diagnosis.

To allow measurement of concentration of a marker of the inflammatory response in a wound, a sample of wound fluid must be added to the assay system. Measurement may either be made in situ, or fluid may be removed from the wound for subsequent analysis. The decision as to which method is used will depend upon the type of wound in question.

For example, in the case of surface-exposed wounds, a clinical swab, dressing, "dipstick" or other biosensor device may be applied directly to the surface of the wound. The device should contain the components of the assay system for measuring the concentration of the marker so that the assay reaction may itself proceed in situ.

The device can then be removed from the wound and the signal measured by the appropriate means. In many cases, a physician may not actually require an accurate assessment of the precise concentration of the marker, but may just wish to know whether there is a sufficient concentration of the marker to warrant prophylactic or curative action as necessary. In these cases, visible assessment of the dressing may be sufficient to allow identification of the specific areas of infection. Unnecessary treatment of healthy granulating tissue can then be avoided.

A dressing that allows mapping of the infected areas of a wound will be preferable in certain instances. Diagnostic wound mapping sheets that could be adapted to the methods of the present invention are described in GB2323166 (application no. GB 9705081.9), filed on 12 Mar. 1997, the entire content of which is hereby incorporated by reference.

Immobilisation of reaction components onto a dipstick, wound mapping sheet or other solid or gel substrate offers the opportunity of performing a more quantitative measurement. For example, in the case of a reaction linked to the generation of a colour the device may be transferred to a spectrometer. Suitable methods of analysis will be apparent to those of skill in the art.

Immobilisation of the reaction components to a small biosensor device will also have the advantage that less of the components (such as enzyme and substrate) are needed. The device will thus be less expensive to manufacture than a dressing that needs to have a large surface area in order to allow the mapping of a large wound area.

Methods for the incorporation of the components of the assay reaction onto a clinical dressing, "dipstick", sheet or other biosensor are routine in the art. See for example Fägerstam and Karlsson (1994) *Immunochemistry*, 949-970.

The concentration of the marker may alternatively be measured in an aqueous assay system. Wound fluid may be extracted directly from the environment of the wound or can be washed off the wound using a saline buffer. The resulting solution can then be assayed for the concentration of the marker in, for example, a test tube or in a microassay plate.

Such a method will be preferable for use in cases in which the wound is too small or too inaccessible to allow access of a diagnostic device such as a dipstick. This method has the additional advantage that the wound exudate sample may be diluted.

It will be clear that an aqueous assay system is more applicable to use in a laboratory environment, whereas a wound dressing containing the necessary reaction components will be more suitable for use in a hospital or domestic environment.

Specific embodiments of the present invention will now be described in more detail, by way of example, with reference to the accompanying drawings, in which:

EXAMPLES

Clinical Study and Patient Selection

All patients enrolled in this study had diabetic foot ulcers of at least 30 days duration and a surface area of at least 1 $cm^2$. Patients were excluded if the target wound showed any signs of infection or if exposed bone with positive osteomyelitis was observed. Additional exclusion criteria included concomitant conditions or treatments that may have interfered with wound healing and a history of non-compliance that would make it unlikely that a patient would complete the study. Nine patients meeting these study criteria were enrolled, and wound fluid collected. Informed consent was obtained from all patients or their authorised representatives prior to study enrolment and the protocol was approved by the Ethics Committee at the participating study centre prior to the commencement of the study.

The study was conducted in accordance with both the Declaration of Helsinki and Good Clinical Practice.

Protein Assay

Total protein present in each extracted wound fluid sample was determined using the Bradford protein assay. The protein binding solution comprises 1 ml Coomassie Brillant Blue stock solution 200 mg-Coomassie Brillant Blue G250, Sigma Chemical Co., dissolved in 50 ml ethanol-90%); 2 ml orthophosphoric acid (85% w/v); in a final volume of 20 ml with distilled water. This solution was filtered (Whatman #1 filter paper) and used immediately. The protein level in a sample wound fluid was measured by mixing 10-µl sample or standard with 190-µl of the protein binding solution in a microtitre well and incubating for 30 mins at ambient temperature prior to reading absorbance at 595 nm. The concentration of protein was estimated from a standard calibration of BSA (bovine serum albumin prepared in distilled water; Sigma Chemical Co.) ranging from 1.0 to 001 mg/ml.

Protease Activity Assays

The levels of neutrophil-derived elastase, plasmin and matrix metalloproteinases present in the wound fluid samples were measured spectrofluorimetrically using substrate activity assays. The substrates comprise short peptides synthesised to mimic the appropriate enzyme cleavage site and contain a fluorescent reporter group which is released upon hydrolysis. Enzyme activity was determined by measuring the rate of production of the fluorimetric compound, 7-amino 4-methyl coumarin. Activity was expressed either as relative fluorescence units per minute (RFU/min) or change in fluorescence when corrected for total protein (RFU/min/mg protein). Each sample was tested times 6 and the average value calculated. The substrate was prepared at 10 mM-stock concentration, and diluted to a working concentration of 0.5 mM in the appropriate assay buffer. The reaction mixture, combined in a microtitre well (black, flat bottomed) comprised 5 µl wound fluid, 175 µl assay buffer and 20 µl substrate (final concentration 50 µM). The microtitre plate was read immediately at 455 nm (excitation 383 nm) and at timed intervals over the next hour, between readings the plate was covered and incubated at 37° C.

Neutrophil-derived elastase-like activity was estimated using the fluorimetric substrate Methoxy-Alanine-Proline-Valine-7-amino 4-methyl coumarin (Bachem UK, Ltd.) solubilised in methanol. The assay buffer required for optimal activity of this enzyme was 0.1M Hepes, pH 7.5 containing 0.5M NaCl and 10% dimethyl sulphoxide.

Plasmin-like activity was measured using Methoxysuccinyl-Alanine-Lysine-Phenylalanine-Lysine 7-amino 4-methyl coumarin (Bachem UK, Ltd.) solubilised in 1 mM-HCl. The assay buffer required for plasmin activity was 25 mM Tris-HCl, pH 8.1 containing 0.5~% triton X-100.

Matrix metalloproteinase-like activity was estimated utilising the substrate Succinyl-Glycine-Proline-Leucine-Glycine-Proline 7-amino 4-methyl coumarin (Bachem, UK, Ltd.) solubilised in methanol. The assay buffer necessary for maximal MMP activity was 40 mM Tris/HCl, pH 7.4 containing 200 mM NaCl and 10 mM $CaCl_2$.

The results of the assays are shown in FIG. 1. Patient 8 had 10-fold more elastase activity and within two days was hospitalised for severe cellulitis/infection.

The above example has been described for the purpose of illustration only. Many other embodiments falling within the scope of the accompanying claims will be apparent to the skilled reader.

The invention claimed is:

1. A method of predicting or diagnosing clinical infection of a chronic wound comprising measuring a concentration of a neutrophil elastase in wound fluid from the chronic wound, comparing the concentration to a basal level concentration of a neutrophil elastase, and determining if the concentration is at or above a level indicative of clinical infection or subsequent progression of the chronic wound to clinical infection; wherein the concentration of the neutrophil elastase is measured by a dip-stick type test; wherein a concentration from about 1.5-fold to about 16.0-fold the basal level concentration is indicative of clinical infection; and wherein a concentration from about 1.5-fold to 9.0-fold the basal level concentration is indicative of subsequent progression to clinical infection.

2. The method according to claim 1 wherein the chronic wound is a chronic ulcer.

3. The method of claim 2 wherein the chronic ulcer is a dermal ulcer, venous ulcer, pressure sore, or decubitis ulcer.

4. The method according to claim 1 wherein the concentration of the neutrophil elastase is measured using an immunological, spectrophotometric, colorimetric, fluorimetric, or radioactive detection based technique.

5. The method of claim 1 wherein the measuring is performed on a sample of the wound fluid that has been removed from the body of a patient.

6. The method of claim 1 wherein the method is for predicting clinical infection of a chronic wound and determining if the concentration is at or above a level indicative of subsequent progression of the chronic wound from non-clinical to clinical infection.

7. The method according to claim 6 wherein the chronic wound is a chronic ulcer.

8. The method of claim 7 wherein the chronic ulcer is a dermal ulcer, venous ulcer, pressure sore, or decubitis ulcer.

9. The method according to claim 6 wherein the concentration of the neutrophil elastase is measured using an immunological, spectrophotometric, colorimetric, fluorometric, or radioactive detection based technique.

10. The method of claim 6 wherein the measuring is performed on a sample of the wound fluid that has been removed from the body of a patient.

* * * * *